(12) United States Patent
Zhuang (10) Patent No.: US 11,247,018 B2
(45) Date of Patent: Feb. 15, 2022

(54) GAS GUIDE TUBE ASSEMBLY, LIQUID STORAGE DEVICE, HUMIDIFIER, AND VENTILATOR

(71) Applicant: BMC MEDICAL CO., LTD., Beijing (CN)

(72) Inventor: Zhi Zhuang, Beijing (CN)

(73) Assignee: BMC Medical Co., Ltd., Beijing (CN)

( * ) Notice: Subject to any disclaimer, the term of this patent is extended or adjusted under 35 U.S.C. 154(b) by 476 days.

(21) Appl. No.: 16/329,276

(22) PCT Filed: Aug. 22, 2017

(86) PCT No.: PCT/CN2017/098382
§ 371 (c)(1),
(2) Date: Feb. 28, 2019

(87) PCT Pub. No.: WO2018/040975
PCT Pub. Date: Mar. 8, 2018

(65) Prior Publication Data
US 2021/0283361 A1    Sep. 16, 2021

(30) Foreign Application Priority Data

Aug. 31, 2016  (CN) .................. 201610782796.X
Aug. 31, 2016  (CN) .................. 201610782799.3

(51) Int. Cl.
*A61M 16/16* (2006.01)
*A61M 16/08* (2006.01)

(52) U.S. Cl.
CPC ........ *A61M 16/16* (2013.01); *A61M 16/0875* (2013.01)

(58) Field of Classification Search
CPC ............... A61M 16/16; A61M 16/109; A61M 16/0875; A61M 16/00; A61M 16/08; A61M 2202/02
See application file for complete search history.

(56) References Cited

U.S. PATENT DOCUMENTS 5,062,145 A * 10/1991 Zwaan .................. A61M 16/16
                                                        392/396
2005/0166917 A1   8/2005 Ahlmen et al.
(Continued)

FOREIGN PATENT DOCUMENTS

CN    204352325 U    5/2015
CN    204521864 U    8/2015
(Continued)

OTHER PUBLICATIONS

European Patent Office, Exended European Search Report dated Jun. 11, 2019, for corresponding European Patent Application No. 17845277.7.
(Continued)

*Primary Examiner* — Kendra D Carter
*Assistant Examiner* — Thomas W Greig
(74) *Attorney, Agent, or Firm* — Duane Morris LLP (57) ABSTRACT

A gas guide tube assembly (200), a liquid storage device (10), a humidifier, and a ventilator. The gas guide tube assembly (200) comprises: a gas outlet guiding tube (210) having a gas inlet port (212) and a gas outlet port (214); and a guide tube (220) having a communication port (222) that communicates with the gas inlet port (212) of the gas outlet guiding tube (210) and a plurality of gas reflux ports (224, 226) that communicate with the communication port (222). The gas guide tube assembly (200), when in use, is disposed in a liquid storage cavity (120) of the humidifier, and the gas outlet port (214) of the gas outlet guiding tube (210) of the gas guide tube assembly (200) communicates with a gas outlet (124) of the liquid storage cavity (120). The present invention can solve to a certain extent a problem of water inhalation into the user due to overflow from the gas outlet (124).

18 Claims, 6 Drawing Sheets

(56) References Cited

U.S. PATENT DOCUMENTS

| | | |
|---|---|---|
| 2007/0230927 A1 | 10/2007 | Kramer |
| 2011/0285038 A1 | 11/2011 | Lin |
| 2015/0059748 A1 | 3/2015 | Hsaio et al. |
| 2015/0283352 A1* | 10/2015 | Karkkainen ........... A61M 11/04 128/203.26 |
| 2016/0022954 A1* | 1/2016 | Bath ................... A61M 16/024 128/203.27 |
| 2016/0184547 A1* | 6/2016 | Leonard ................ A61M 16/20 128/203.25 |

FOREIGN PATENT DOCUMENTS

| | | |
|---|---|---|
| CN | 104941047 A | 9/2015 |
| CN | 106237478 A | 12/2016 |
| CN | 106310475 A | 1/2017 |
| CN | 206285330 U | 6/2017 |
| CN | 206350858 U | 7/2017 |
| CN | 104415474 A | 3/2018 |
| JP | 2016063877 A | 4/2018 |

OTHER PUBLICATIONS

Indian Patent Office, Examination Report dated Jul. 8, 2020, for corresponding Indian Patent Application No. 201947012508.

* cited by examiner

GAS GUIDE TUBE ASSEMBLY, LIQUID STORAGE DEVICE, HUMIDIFIER, AND VENTILATOR

CROSS REFERENCE TO RELATED APPLICATIONS

The present application is a National Stage Application, filed under 35 U.S.C. 371, of International Patent Application No. PCT/CN 2017/098382, filed on Aug. 22, 2017, which claims for the priority of the Chinese Patent Applications No. 201610782799.3 and No. 201610782796.X, both filed on Aug. 31, 2016, the content of each of which is incorporated here by reference in entirety.

FIELD OF THE INVENTION

The present invention relates to the field of respiratory therapy equipment, particularly to a gas guide tube assembly for the humidifier of a ventilator, a liquid storage device having the gas guide tube assembly, a humidifier having the liquid storage device, and a ventilator having the humidifier.

BACKGROUND OF THE INVENTION

Presently, continuous positive airway pressure (CPAP) ventilation with a ventilator is the main treatment for sleep apnea syndrome (such as severe snoring) and other diseases. Wherein, a humidifier is an important component of the ventilator, and has functions of warming up and humidifying the gas to increase the moisture content in the gas so that the gas inhaled by the user is warm and humid, and thereby reduce the stimulation of cold and dry gas to the respiratory mucosa, and improve the comfort of the user.

A humidifier usually comprises a water tank and a heating element. The heating element transfers heat to the water in the water tank to accelerate water evaporation and thereby output gas at appropriate temperature and humidity to the user. However, some users need to move the humidifier during use. In the moving process, the water in the water tank may overflow from the gas outlet or gas inlet of the water tank, and the overflow water may enter into the breathing mask through the transfer tube, resulting in water inhalation into the user; or the overflow water may enter into the main unit of the machine, causing degraded performance of the main unit or even damage of the electric elements in the main unit.

Therefore, it is necessary to a provide a gas guide tube assembly for the humidifier of a ventilator, a liquid storage device having the gas guide tube assembly, a humidifier having the liquid storage device, and a ventilator having the humidifier, to solve the overflow problem in existing humidifiers.

SUMMARY OF THE INVENTION

To completely or at least partially solve the problems incurred by overflow from the gas outlet in existing humidifiers in the prior art, the present invention provides a gas guide tube assembly for humidifier. The gas guide tube assembly comprises: a gas outlet guiding tube having a gas inlet port and a gas outlet port; and a guide tube having a communication port that communicates with the gas inlet port of the gas outlet guiding tube and a plurality of gas reflux ports that communicate with the communication port.

Preferably, the ports of the gas guide tube assembly include the gas inlet port and the gas outlet port of the gas outlet guiding tube, and the plurality of gas reflux ports, wherein in a first direction, at least one of the gas inlet port and the gas outlet port of the gas outlet guiding tube is flush with or higher than the other ports among the ports.

Preferably, in a first direction, the communication port of the guide tube is higher than the gas reflux ports, and/or the gas inlet port of the gas outlet guiding tube is lower than the gas outlet port of the gas outlet guiding tube.

Preferably, the guide tube is a straight guide tube having two gas reflux ports.

Preferably, the gas guide tube assembly further comprises a gas inlet guide tube having a gas inlet port and a gas outlet port, wherein, in a first direction, the gas inlet port of the gas inlet guide tube is higher than the gas outlet port of the gas inlet guide tube.

Preferably, the gas outlet port of the gas inlet guide tube is below the guide tube, and the opening of the gas outlet port of the gas inlet guide tube is downward.

Preferably, the gas guide tube assembly further comprises a connector, the connector fixes the gas outlet port of the gas outlet guiding tube and the gas inlet port of the gas inlet guide tube together and is configured to connect the gas guide tube assembly to the liquid storage cavity of the humidifier.

Preferably, the guide tube is provided with a separating rib therein, the separating rib is arranged in the lower part of the flow path in the guide tube and configured to separate the lower flow path in the guide tube.

Preferably, the separating rib is disposed at the communication port of the guide tube.

According to another aspect of the present invention, the present invention provides a liquid storage device for humidifier. The liquid storage device comprises: a casing assembly with an liquid storage cavity formed internally, the liquid storage cavity have a gas inlet and a gas outlet; and the gas guide tube assembly described above, wherein, the gas guide tube assembly is disposed in the liquid storage cavity and connected to the casing assembly, the gas outlet port of the gas outlet guiding tube of the gas guide tube assembly communicates with the gas outlet, and the gas reflux ports of the gas guide tube assembly are higher than the maximum fillable level in the liquid storage cavity.

Preferably, a gas inlet cavity and a gas outlet cavity are formed in the casing assembly, wherein, the gas inlet cavity has a first gas inlet communicating with the liquid storage cavity and a second gas inlet communicating with the exterior of the liquid storage device; and the gas outlet cavity has a first gas outlet communicating with the liquid storage cavity and a second gas outlet communicating with the exterior of the liquid storage device.

Preferably, both the gas inlet cavity and the gas outlet cavity are adjacent to the liquid storage cavity.

Preferably, the casing assembly comprises an upper casing assembly and a lower casing assembly, the upper casing assembly is removably or pivotally connected to the lower casing assembly, and the upper casing assembly and the lower casing assembly jointly form the liquid storage cavity, the gas inlet cavity, and the gas outlet cavity.

Preferably, the liquid storage cavity comprises a first sub-cavity in the lower casing assembly configured to accommodate liquid and a second sub-cavity in the upper casing assembly.

Preferably, the upper casing assembly has a first fitting surface, the lower casing assembly has a second fitting surface, and the first fitting surface and the second fitting surface are asymmetric curved surfaces fitted with each other.

Preferably, both the first fitting surface and the second fitting surface comprise a first bevel surface and a second bevel surface that are inclined downward from a central part to opposite sides and are arranged asymmetrically.

Preferably, the gas inlet cavity and the gas outlet cavity are formed by separating with a first baffle plate and a second baffle plate in the casing assembly, wherein the first baffle plate is disposed between the gas inlet cavity, the gas outlet cavity and the liquid storage cavity, the second baffle plate is disposed between the gas inlet cavity and the gas outlet cavity, and both the first gas inlet and the first gas outlet are arranged on the first baffle plate.

Preferably, the second gas inlet is higher than the first gas inlet, and/or the second gas outlet is higher than the first gas outlet.

Preferably, the second gas inlet and the second gas outlet are arranged on a first side surface of the liquid storage device, and the first side surface is connected via a bevel surface to a side surface of the liquid storage device that is adjacent to the first side surface.

Preferably, the casing assembly comprises a seal ring disposed between the upper casing assembly and the lower casing assembly, the inner circumference of the seal ring extends into the liquid storage cavity, and the gas reflux ports of the guide tube are right above the portion of the seal ring that extends into the liquid storage cavity.

According to another aspect of the present invention, the present invention provides a humidifier that comprises a heating element and the liquid storage device described above, wherein, the heating element is disposed under the liquid storage cavity of the liquid storage device.

According to a still another aspect of the present invention, the present invention provides a ventilator that comprises the humidifier described above.

The gas guide tube assembly provided in the present invention may be disposed in the liquid storage cavity of a humidifier, and the gas outlet port of a gas outlet guiding tube of the gas guide tube assembly communicates with a gas outlet of the liquid storage cavity. Since a guide tube is connected with the gas inlet port of a gas outlet guiding tube of the gas guide tube assembly, the gas is guided via the guide tube to flow into the gas inlet port of the gas outlet guiding tube; in addition, the guide tube has a plurality of gas reflux ports, so that the liquid will flow out via the other gas reflux ports even if the liquid flows in via one gas reflux port incurred by swaying of the liquid storage cavity, and thereby the possibility of liquid flowing into the gas inlet port of the gas outlet guiding tube is decreased. Furthermore, owing to the existence of the gas outlet guiding tube and the guide tube, the flow path of the gas in the liquid storage cavity is lengthened, so that the gas can be mixed extensively with the vapor produced through evaporation, and thereby the outflow gas has expected humidity and temperature.

The concept of a series of simplified forms is introduced in this section, and will be further detailed in the detailed description of the embodiments. The content of the present invention is not intended to define key features and essential technical features of the technical scheme claimed for protection or intended to define the protection scope of the technical scheme claimed for protection.

Hereunder the advantages and features of the present invention will be detailed with reference to the accompanying drawings.

BRIEF DESCRIPTION OF DRAWINGS

The following figures and presented here as a part of the present invention to facilitate the understanding on the present invention. The figures show embodiments and provide description of the present invention to interpret the principle of the present invention. In the figures.

DETAILED DESCRIPTION OF THE EMBODIMENTS

In the following description, many details are provided to facilitate thorough understanding on the present invention. However, those skilled in the art should appreciate that the following description only exemplarily describes some preferred embodiments of the present invention, and the present invention can be implemented without one or more of such details. Besides, to avoid confusion with the present invention, some technical features that are well known in the art are not detailed here.

According to an aspect of the present invention, the present invention provides a gas guide tube assembly for humidifier and a liquid storage device having the gas guide tube assembly. FIGS. 1-9 shows the entire liquid storage device and the components or parts included in the liquid storage device, such as the gas guide tube assembly, upper casing, and lower casing, etc., viewed from different angles. To make the positions and functions of those components or parts in the liquid storage device understood better, first, the liquid storage device will be described generally, so that the present invention can be understood thoroughly.

As shown in FIGS. 1-4, the liquid storage device 10 comprises a casing assembly 100 and a gas guide tube assembly 200.

Figure 1:
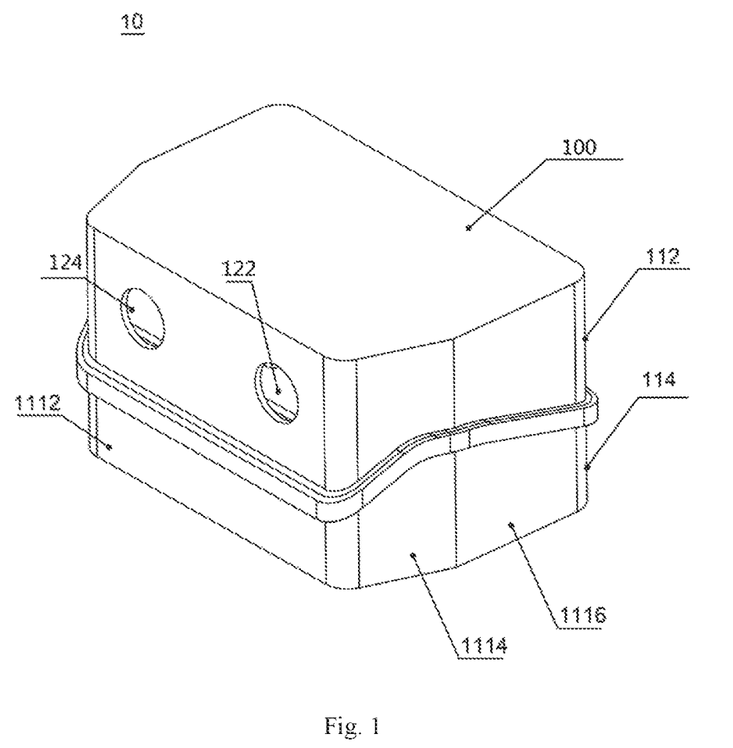
FIG. 1 is a schematic structural diagram of the liquid storage device according to an embodiment of the present invention.
Figure 2:
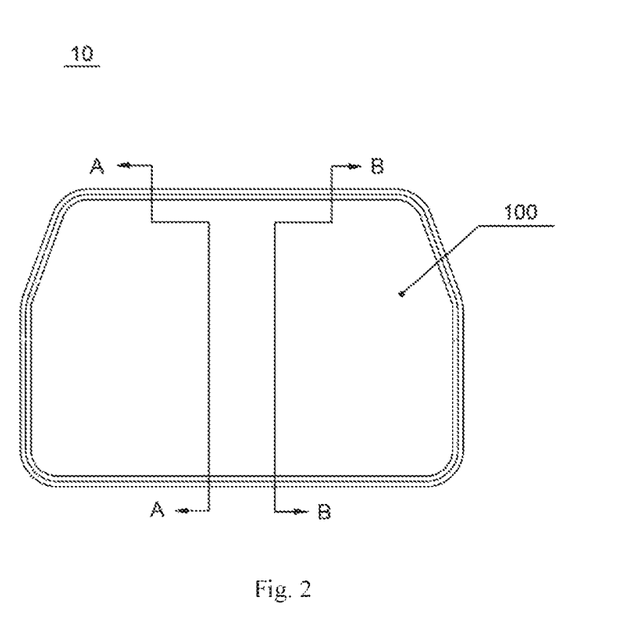
FIG. 2 is a top view of the liquid storage device shown in FIG. 1.
Figure 3A:
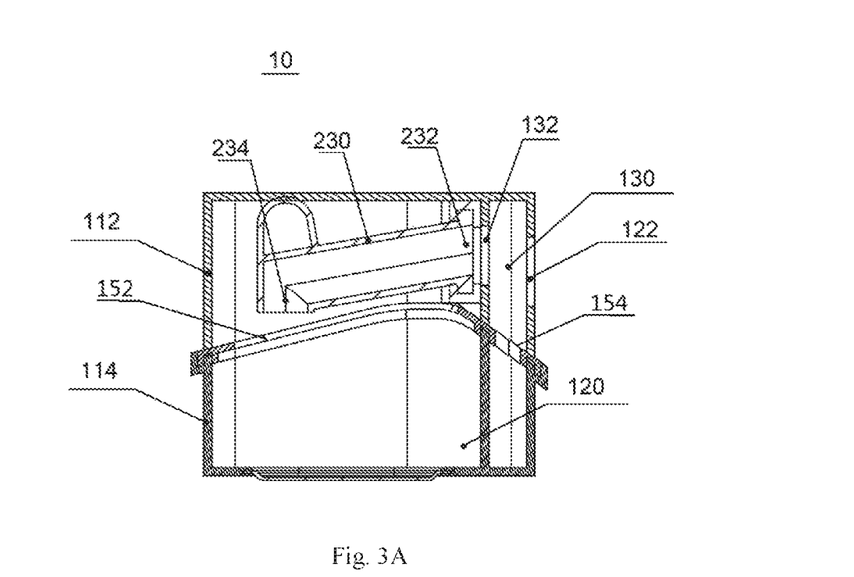
FIG. 3A is a sectional view of the liquid storage device along the line A-A in FIG. 2, illustrating the gas inlet cavity and its gas inlet.
Figure 3B:
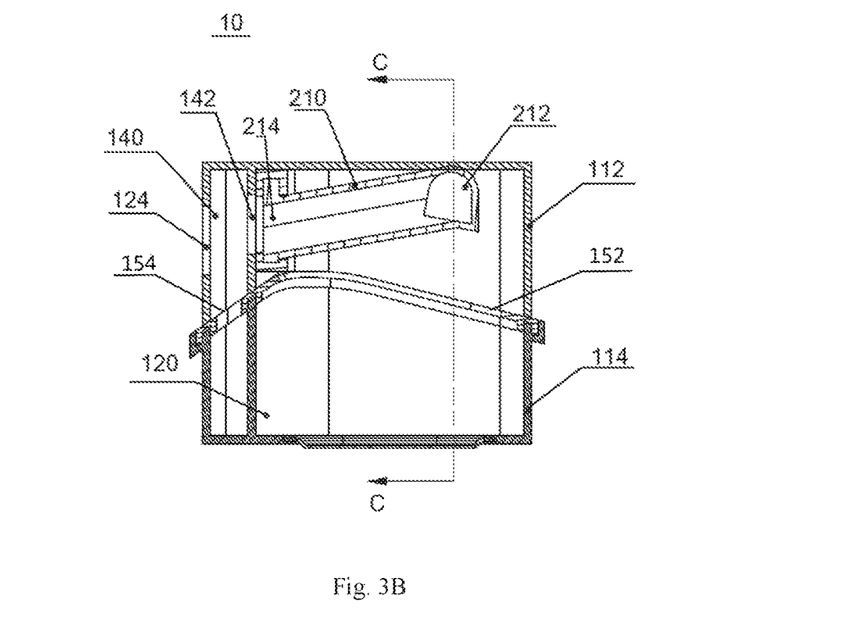
FIG. 3B is a sectional view of the liquid storage device along the line B-B in FIG. 2, illustrating the gas outlet cavity and its gas outlet.

A plurality of cavities that are sealed with respect to each other are formed in the casing assembly 100. Those cavities communicate with each other via required inlets and outlets; except that, those cavities are gas-tight separately. As shown in FIGS. 3A and 3B, those cavities include a liquid storage cavity 120, a gas inlet cavity 130, and a gas outlet cavity 140. Wherein, the liquid storage cavity 120 has a second gas inlet 122 and a second gas outlet 124. In the humidifying process, the liquid storage cavity 120 is in fluid transfer with the exterior only via the second gas inlet 122 and the second gas outlet 124.

The liquid storage cavity 120 is configured to store liquid. The liquid comprises water that is used to humidify the gas inhaled into the respiratory tract of the user. The liquid may further comprise other substances, such as dissoluble drug, etc. The liquid storage cavity 120 may have a liquid injection port, via which the liquid is injected into the liquid storage cavity 120. The liquid injection port may be at the top or on the top part of a side surface of the liquid storage cavity 120. Usually the liquid storage cavity 120 is not fully filled with the fluid, that is to say, the liquid storage cavity 120 usually has a maximum fillable level. The maximum fillable level refers to a maximum allowable level of liquid filled in the liquid storage cavity 120. If the liquid exceeds that level, the liquid may overflow from the liquid storage cavity 120 in some cases (e.g., when the liquid storage device moves), owing to the existence of the gas inlet and the gas outlet as described below. In addition, the space in the upper part of the liquid storage cavity 120 is further used to accommodate the vapor produced through the evaporation and mix the vapor with respiratory gas. Thus, in the case that the liquid injection port is arranged at the top of the liquid storage cavity 120, advantageously a scale mark is provided on the liquid storage cavity 120 to indicate the maximum fillable level of the liquid storage cavity 120 to the user. In the case that the liquid injection port is arranged on the top part of a side surface of the liquid storage cavity 120, the maximum fillable level of the liquid storage cavity 120 may be limited by means of the position of the liquid injection port.

In a preferred embodiment, the casing assembly 100 may comprise an upper casing assembly 112, a lower casing assembly 114, and a seal ring 116 between the upper casing assembly 112 and the lower casing assembly 114. The upper casing assembly 112 is removably connected to the lower casing assembly 114. As shown in the exploded view in FIG. 4 and the schematic structural diagram s in FIGS. 5 and 6, when the upper casing assembly 112 and the lower casing assembly 114 are coupled to each other, the seal ring 116 can seal the clearance between the upper casing assembly 112 and the lower casing assembly 114, to ensure relative gas tightness of the liquid storage cavity 120, the gas inlet cavity 130, and the gas outlet cavity 140 in the casing assembly 100. Optionally, the seal ring 116 may be arranged on either or both of the upper casing assembly 112 and the lower casing assembly 114. In this embodiment, the liquid storage cavity 120 is formed jointly by the upper casing assembly 112 and the lower casing assembly 114. Therefore, when the upper casing assembly 112 is opened, the liquid storage cavity 120 will be opened, and the liquid can be injected into the liquid storage cavity 120. An advantage of such a structure of the casing assembly 100 is that the apparatus can be disassembled and cleaned conveniently at any time, and the liquid can be injected into the liquid storage cavity 120 directly when the upper casing assembly 112 is opened, without arranging an additional liquid injection port on the liquid storage cavity 120. Besides, the structure can facilitate manufacturing. Optionally, a locking structure may be provided between the upper casing assembly 112 and the lower casing assembly 114. The locking structure locks up the upper casing assembly 112 and the lower casing assembly 114 when the upper casing assembly 112 and the lower casing assembly 114 are coupled to each other, to ensure gas tightness between them.

Furthermore, in the case that the casing assembly 100 comprises the two parts as described above, the two parts may be pivotally connected together. For example, the upper casing assembly 112 and the lower casing assembly 114 may be connected via a hinge structure between them, so that the upper casing assembly 112 can be pivotally opened with respect to the lower casing assembly 114. In this embodiment, the hinge structure preferably is arranged at the side where the gas inlet cavity 130 and the gas outlet cavity 140 are located, so that the liquid storage cavity 120 is exposed first when the upper casing assembly 112 is opened, and the liquid can be injected into the liquid storage cavity 120 conveniently and can be prevented from entering into the gas inlet cavity 130 and the gas outlet cavity 140 accidentally.

Figure 4:
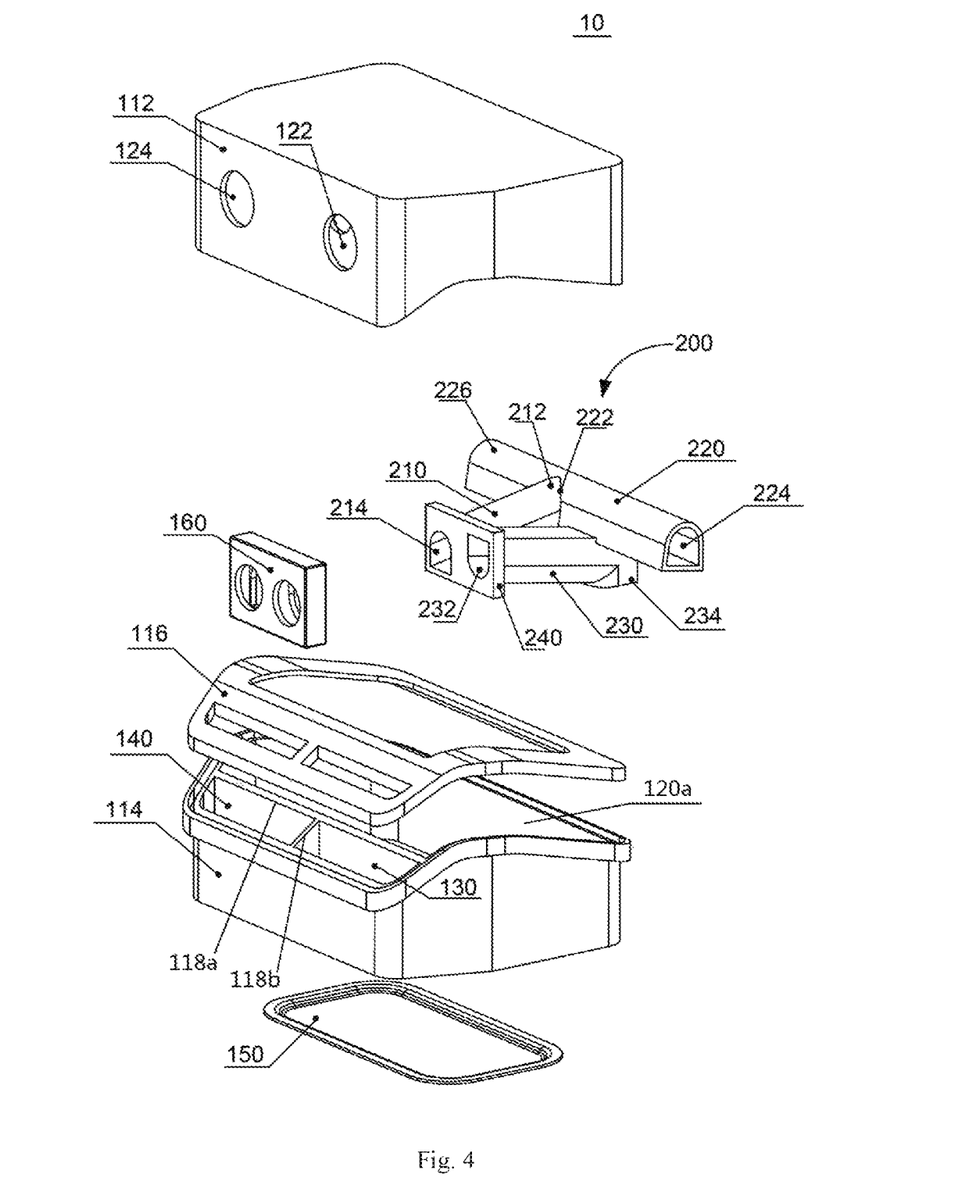
FIG. 4 is an exploded view of the liquid storage device according to an embodiment of the present invention.

As shown in FIGS. 3A-3B and 4, the gas inlet cavity 130 and the gas outlet cavity 140 may communicate with the liquid storage cavity 120 via a first gas inlet 132 and a first gas outlet 142, and the gas inlet cavity 130 and the gas outlet cavity 140 are configured to collect the overflow liquid from the liquid storage cavity 120 to prevent the liquid from over-flowing out of the liquid storage device 10 and entering into the main unit or the breathing mask. Optionally, the gas inlet cavity 130 and the gas outlet cavity 140 may be formed jointly by the upper casing assembly 112 and the lower casing assembly 114. Thus, the cavities can be cleaned conveniently when the upper casing assembly 112 is opened, and the structure is easy to manufacture.

For example, as shown in FIG. 4, the internal space of the casing assembly 100 may be separated by means of a first baffle plate 118a and a second baffle plate 118b into three cavities, i.e., the liquid storage cavity 120, the gas inlet cavity 130, and the gas outlet cavity 140. The liquid storage cavity 120 separated by the first baffle plate 118a occupied a major part of the internal space of the casing assembly 100. The first baffle plate 118a is arranged between the liquid storage cavity 120 and the gas inlet cavity 130, the gas outlet cavity 140. The second baffle plate 118b separates the remaining minor part into the gas inlet cavity 130 and the gas outlet cavity 140. The second baffle plate 118b is arranged between the gas inlet cavity 130 and the gas outlet cavity 140. The upper casing assembly 112 and the lower casing assembly 114 may respectively comprise a part of the first baffle plate 118a and the second baffle plate 118b. The embodiment shown in FIGS. 4-6 only provides an arrangement of the liquid storage cavity 120, the gas inlet cavity 130, and the gas outlet cavity 140 exemplarily. In practice, the three cavities may be in a different arrangement. Therefore, the illustrated embodiment is only exemplary rather than limitative. However, preferably, both the gas inlet cavity 130 and the gas outlet cavity 140 are adjacent to the liquid storage cavity 120. Thus, the internal design of the casing assembly 100 is more compact, and the size of the entire apparatus can be decreased.

Figure 5:
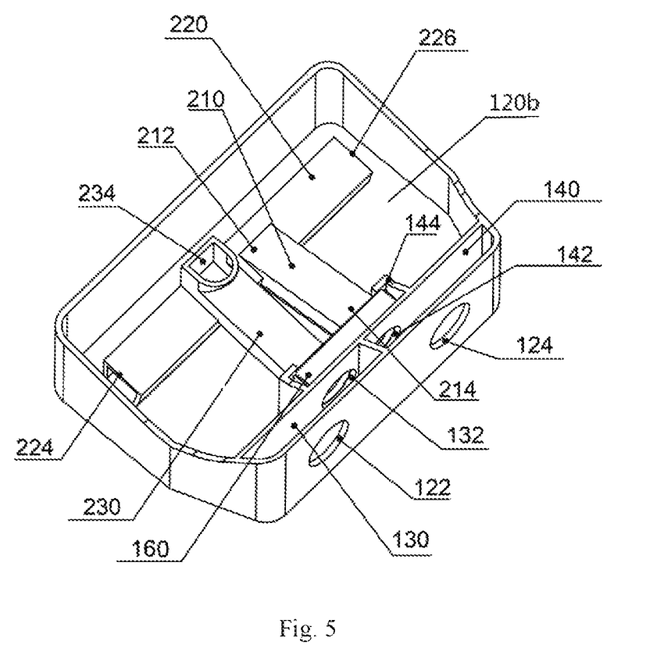
FIG. 5 is a schematic structural diagram of the upper casing assembly according to an embodiment of the present invention when viewed from the bottom.

Please see FIG. 5. The gas inlet cavity 130 may have a first gas inlet 132 and a second gas inlet 122. The first gas inlet 132 communicates with the liquid storage cavity 120, so that the gas inlet cavity 130 collects the overflow liquid from the first gas inlet 132, and thereby avoid liquid outflow via the second gas inlet 122. The first gas inlet 132 may be arranged on a side wall of the gas inlet cavity 130. For example, it may be arranged on the first baffle plate 118a (see FIG. 5). The second gas inlet 122 communicates with the exterior of the liquid storage device. The second gas inlet 122 may be arranged in relation to the first gas inlet 132. For example, the second gas inlet 122 may be arranged on an outer wall of the casing assembly, so that it can communicate with a gas supply port of the main unit of the ventilator. The respiratory gas (e.g., air) blasted by the main unit is supplied into the liquid storage device 10 continually via the second gas inlet 122, and then enters into the liquid storage cavity 120 via the first gas inlet 132 and is mixed with the vapor generation through the evaporation. If the liquid overflows via the first gas inlet 132 from the liquid storage cavity 120 by accident, the gas inlet cavity 130 can collect that part of liquid to prevent the overflow liquid from entering into the main unit via the second gas inlet 122. Preferably, the second gas inlet 122 is higher than the first gas inlet 132, so that even the overflow liquid fills up the gas inlet cavity 130, it will returns to the liquid storage cavity 120 via the first gas inlet 132 and can't flow out of the second gas inlet 122. In the embodiment in which the casing assembly 100 comprises the upper casing assembly 112 and the lower casing assembly 114, both the first gas inlet 132 and the second gas inlet 122 may be arranged on the upper casing assembly 112. Thus, both gas inlets can be higher than the maximum fillable level of the liquid storage cavity 120, and no liquid overflow will occur unless the liquid storage device is tilted.

The gas outlet cavity 140 may have a first gas outlet 142 and a second gas outlet 124. The first gas outlet 142 communicates with the liquid storage cavity 120, so that the gas cavity 140 collects the overflow liquid from the first gas outlet 142 and thereby prevents the liquid from over-flowing out of the second gas outlet 124. The first gas outlet 142 may be arranged on a side wall of the gas outlet cavity 140. For example, the first gas outlet 142 may be arranged on the first baffle plate 118a (see FIG. 5). The second gas outlet 124 communicates with the exterior of the liquid storage device. The second gas outlet 124 may be arranged in relation to the first gas outlet 142. For example, the second gas outlet 124 may be arranged on an outer wall of the casing assembly, so that it can communicate with a user interface (e.g., a breathing mask). The respiratory gas blasted by the main unit is mixed extensively with the vapor generated through the evaporation in the liquid storage cavity 120, and then leaves the liquid storage cavity 120 via the first gas outlet 142, passes through the gas outlet cavity 140, and then flows out from the second gas outlet 124 and enters into the user interface. If the liquid overflows via the first gas outlet 142 from the liquid storage cavity 120 by accident, the gas outlet cavity 140 can collect that part of liquid to prevent that part of liquid from over-flowing out of the second gas outlet 124 and entering into the user interface. Preferably, the second gas outlet 124 is higher than the first gas outlet 142, so that even the overflow liquid fills up the gas outlet cavity 140, it will returns to the liquid storage cavity 120 via the first gas outlet 142 and can't flow out of the second gas outlet 124. In the embodiment in which the casing assembly 100 comprises the upper casing assembly 112 and the lower casing assembly 114, both the first gas outlet 142 and the second gas outlet 124 may be arranged on the upper casing assembly 112. Thus, both gas outlets can be higher than the maximum fillable level of the liquid storage cavity 120, and no liquid overflow will occur unless the liquid storage device is tilted.

As shown in FIG. 4, to accelerate evaporation of the liquid in the liquid storage cavity 120, preferably a heat transfer plate 150 is provided on the bottom of the liquid storage cavity 120. For example, a bottom opening may be arranged on the casing assembly at the bottom of the liquid storage cavity 120. The heat transfer plate 150 is embedded in the bottom opening in a sealed manner. Optionally, the heat transfer plate 150 may be coupled to the bottom opening of the casing assembly, and a seal ring, sealant, or the like may be arranged between the heat transfer plate 150 and the bottom opening. The humidifier for ventilator may comprises a heating element and the liquid storage device provided in the present invention. When the liquid storage device is mounted in the humidifier, the heat transfer plate 150 on the bottom of the liquid storage cavity 120 will come into contact with the heating element. The heat transfer plate 150 transfers the heat generated by the heating element to the liquid in the liquid storage device, so that the liquid is evaporated. In other embodiments, a heating rod may be arranged directly in the liquid storage cavity 120, to heat up the liquid in the liquid storage cavity 120 directly with the heating rod.

The heat transfer plate 150 and the heating element may have a structure that is known or may occur in the future in the art. The improvement in the present invention doesn't lies in the heat transfer plate 150 and the heating element themselves. Therefore, the heat transfer plate 150 and the heating element will not be further detailed here.

As described above, the casing assembly 100 preferably comprises two parts (i.e., the upper casing assembly 112 and the lower casing assembly 114). In that case, the liquid storage cavity 120 may comprise a first sub-cavity 120a and a second sub-cavity 120b. The first sub-cavity 120a is located in the lower casing assembly 114 and configured to accommodate liquid. The second sub-cavity 120b is located in the upper casing assembly 112. The second sub-cavity 120b mainly provides a space that accommodates the vapor produced through the evaporation so that the vapor can be mixed extensively with the respiratory gas. The first sub-cavity 120a limits the maximum fillable level of the liquid storage cavity 120. When the liquid is filled, as long as the first sub-cavity 120a is filled up, the excessive liquid will flow out automatically; then, the upper casing assembly 112 and the lower casing assembly 114 may be coupled to each other. Thus, the user doesn't have to pay close attention to prevent the level in the liquid storage cavity 120 from exceeding the maximum fillable level whenever the liquid is filled. Therefore, it is very convenience to use. In the illustrated embodiment, the upper casing assembly 112 and the lower casing assembly 114 generally occupy half of the total volume of the casing assembly 100 respectively. Thus, the first sub-cavity 120a and the second sub-cavity 120b are generally in the same volume, or the volume of the second sub-cavity 120b is slightly greater than the volume of the first sub-cavity 120a. However, in other embodiments that are not shown, the volume ratio of the first sub-cavity 120a to the second sub-cavity 120b may be generally ⅓ or ¼, etc. Those skilled in the art may select the volume ratio of the first sub-cavity 120a to the second sub-cavity 120b as required and design the structure of the upper casing assembly 112 and the lower casing assembly 114 accordingly.

Preferably, as shown in FIGS. 3A-3B, the upper casing assembly 112 has a first fitting surface (see the bottom surface of the upper casing assembly 112), and the lower casing assembly 114 has a second fitting surface (see the top surface of the lower casing assembly 114). The first fitting surface and the second fitting surface may be asymmetric curved surfaces fitted with each other. The fitting here refers to that the first fitting surface and the second fitting surface match each other when the upper casing assembly 112 and the lower casing assembly 114 are coupled to each other, to ensure sealing between the upper casing assembly 112 and the lower casing assembly 114. The first fitting surface and the second fitting surface are designed as asymmetric curved surfaces to prevent reverse fitting when the first fitting surface and the second fitting surface are fitted together. In the case of reverse fitting, the liquid storage device can't attain the effect of preventing overflow. In a preferred embodiment, both the first fitting surface and the second fitting surface may comprise a first bevel surface 152 and a second bevel surface 154, which are inclined downward respectively from their central part to opposite sides. The first bevel surface 152 and the second bevel surface 154 are arranged asymmetrically. The two opposite sides may comprise a side where the gas inlet and the gas outlet are provided and a side opposite to the former side. In that case, the first bevel surface 152 generally corresponds to the position of the liquid storage cavity 120, and the second bevel surface 154 generally corresponds to the position of the gas inlet cavity 130 and the gas outlet cavity 140. Optionally, the two opposite sides further comprise another group of opposite sides (not shown). In that case, the first bevel surface generally corresponds to the position of one part of the liquid storage cavity 120 and the gas inlet cavity 130, and the second bevel surface generally corresponds to the position of the other part of the liquid storage cavity and the gas outlet cavity. With the design of the first bevel surface and the second bevel surface that are inclined downward from the central part to two sides, on one hand, the maximum fillable level of the liquid storage cavity 120 can be limited mandatorily; on the other hand, in an embodiment in which the upper casing assembly 112 and the lower casing assembly 114 are pivotally connected with each other, a hinge structure may be mounted more conveniently. Specifically, the hinge structure may be arranged at the lower part of the first bevel surface or the second bevel surface, so as to avoid mutual interference between the upper casing assembly 112 and the lower casing assembly 114 during pivoting at the side where the hinge structure is mounted.

In the liquid storage device for humidifier provided in the present invention, by providing a gas inlet cavity and a gas outlet cavity that communicate with the liquid storage cavity, the gas inlet cavity and the gas outlet cavity can collect overflow liquid from the first gas inlet and the first gas outlet of the liquid storage cavity, the gas inlet cavity can prevent the liquid from over-flowing out from the second gas inlet, and the gas outlet cavity can prevent the liquid from over-flowing out from the second gas outlet. Thus it is seen: the liquid storage device provided in the present invention has an excellent overflow prevention effect.

Hereunder the gas guide tube assembly 200 will be detailed with reference to the accompanying drawings. As shown in FIG. 4, the gas guide tube assembly 200 may comprise a gas outlet guiding tube 210 and a guide tube 220. The gas guide tube assembly 200 is intended to be disposed in the liquid storage cavity 120.

The gas outlet guiding tube 210 has a gas inlet port 212 and a gas outlet port 214. The gas outlet guiding tube 210 is disposed in the liquid storage cavity 120 of the humidifier. The gas outlet port 214 of the gas outlet guiding tube 210 is configured to directly or indirectly communicate with the second gas outlet 124 of the liquid storage cavity 120. The gas outlet port 214 of the gas outlet guiding tube 210 is connected to the first gas outlet 142, as shown in FIG. 3B, the humidified gas passes through the gas outlet cavity 140 and then is transferred to a user interface, and the gas outlet port 214 indirectly communicates with the second gas outlet 124 of the liquid storage cavity 120. In an embodiment in which no gas outlet cavity 140 is provided, the gas outlet port 214 of the gas outlet guiding tube 210 may be directly connected to the second gas outlet 124 of the liquid storage cavity 120. The gas outlet port 214 of the gas outlet guiding tube 210 preferably is removably connected to the first gas outlet 142 or the second gas outlet 124, so that it can be removed and replaced conveniently. For example, a socket may be arranged at the first gas outlet 142 or the second gas outlet 124, and the gas outlet port 214 of the gas outlet guiding tube 210 may be inserted into the socket. FIGS. 4 and 5 show the situation that a socket 144 is arranged at the first gas outlet 142. Thus, they can be connected via a socket joint. To ensure gas tightness of the connection, a sealing element 160 may be provided between them. In other embodiments that are not shown, the gas outlet port 214 of the gas outlet guiding tube 210 may be connected to the first gas outlet 142 in a different way. Different possible connection means are not enumerated and described anymore here.

The guide tube 220 is configured to guide the gas to flow into the gas inlet port 212 of the gas outlet guiding tube 210. The guide tube 220 has a communication port 222 that communicates with the gas inlet port 212 of the gas outlet guiding tube 210 and a plurality of gas reflux ports 224 and 226 that communicate with the communication port 222, as shown in FIGS. 4-5. The communication port 222 may be located at the central part of the guide tube 220. The plurality of gas reflux ports 224 and 226 may be located at the ends of the guide tube 220. The communication port 222 communicates with the gas inlet port 212 of the gas outlet guiding tube 210. The gas reflux ports 224 and 226 of the guide tube 220 communicate with the liquid storage cavity 120. Thus, the humidified gas in the liquid storage cavity 120 reaches to the gas outlet port 214 of the gas outlet guiding tube 210 from the plurality of gas reflux ports 224 and 226 via the communication port 222. The plurality of gas reflux ports 224 and 226 are higher than the maximum fillable level of the liquid storage cavity 120. The humidified gas enters into the gas outlet guiding tube 210 via the gas reflux ports 224 and 226 of the guide tube 220, and then passes through the gas outlet cavity 140 and is discharged. The guide tube 220 lengthens the circulation path of the gas in the liquid storage cavity 120, so that the gas has enough time and travel distance to contact with the vapor to attain a purpose of extensive humidification and provide more humid and comfortable gas to the user.

To attain an effect of overflow prevention, at least one of the gas inlet port 212 and the gas outlet port 214 is flush with or higher than the other ports among the ports included in the gas guide tube assembly 200. The ports of the gas guide tube assembly 200 include the gas inlet port 212 and the gas outlet port 214 of the gas outlet guiding tube 210, and the plurality of gas reflux ports 224 and 226. That is to say, among the gas inlet port 212, the gas outlet port 214, and the plurality of gas reflux ports 224 and 226, generally there are two situations: I. The gas inlet port 212 or the gas outlet port 214 is flush with or higher than the other ports, including two scenarios: a) the gas inlet port 212 is higher than the other ports (including the gas outlet port 214 and the gas reflux ports 224 and 226), i.e., $H_{Inlet} \geq H_{Outlet}$ and $H_{Inlet} \geq H_{Reflux}$; b) the gas outlet port 214 is higher than the other ports (including the gas inlet port 212 and the gas reflux ports 224 and 226), i.e., $H_{Outlet} \geq H_{Inlet}$ and $H_{Outlet} \geq H_{Reflux}$; II. The gas inlet port 212 and the gas outlet port 214 are at the same level, and are flush with or higher than the other ports, $H_{Inlet} = H_{Outlet} \geq H_{Reflux}$. Wherein, $H_{Inlet}$, $H_{Outlet}$, and $H_{Reflux}$, refer to the height of the gas inlet port 212, the height of the gas outlet port 214, and the height of the gas reflux ports 224 and 226 respectively. Both of the above-mentioned situations include the scenario of $H_{Inlet} = H_{Outlet} = H_{Reflux}$. Though the problem of overflow prevention can be solved to some extent in that scenario, the effect may be slightly inferior to the effects in other scenarios. By adding some protective devices, the liquid can be prevented from entering into the gas inlet port 212. An embodiment of such a protective device will be described in the following text. Therefore, preferably, $H_{Inlet}$, $H_{Outlet}$, and $H_{Reflux}$ are not equal to each other.

In the illustrated embodiment, in the case that the gas inlet port 212 of the gas outlet guiding tube 210 is higher than the gas outlet port 214 of the gas outlet guiding tube 210, the liquid in the liquid storage cavity 120 can be prevented from entering into the gas inlet port 212 to some extent. Further preferably, in such a case, advantageously some protective devices are added (as described below) to prevent the liquid from entering into the gas inlet port 212. Or, the gas reflux ports 224 and 226 may be arranged to be lower than the gas inlet port 212. Or, the above-mentioned means may be used in combination.

In a group of embodiments that are not shown, in the case that the gas inlet port 212 of the gas outlet guiding tube 210 is lower than the gas outlet port 214 of the gas outlet guiding tube 210, even if some liquid enters into the gas inlet port 212, the liquid will return to the liquid storage cavity 120 from the gas inlet port 212 under the gravity action. Therefore, that scheme is more preferred relatively. Further preferably, some protective devices (as described below) may be added and/or the gas reflux ports 224 and 226 may be arranged to be lower than the gas inlet port 212.

In another group of embodiments that are not shown, the gas inlet port 212 of the gas outlet guiding tube 210 may be flush with the gas outlet port 214 of the gas outlet guiding tube 210, but both of them are higher than the gas reflux ports 224 and 226. In that case, even if some liquid enters into the gas reflux ports 224 and 226, the liquid will return to the liquid storage cavity 120 under the gravity action rather than enter into the gas outlet guiding tube 210.

It should be noted that all of the terms related with the orientations of the gas guide tube assembly in the present invention, such as "higher", "lower", "upper", "lower", etc., are described with respect to the gas guide tube assembly in the first direction shown in FIG. 4. As shown in FIG. 4, the first direction is the direction in which the gas guide tube assembly is mounted onto the humidifier, i.e., the direction of the gas guide tube assembly when the gas guide tube assembly is used normally.

In the illustrated embodiment, the guide tube 220 is a straight tube and has two gas reflux ports. The guide tube 220 may generally perpendicular to the gas outlet guiding tube 210. If the liquid storage device 10 filled with liquid is swayed left and right so that one of the gas reflux ports of the guide tube 220 is below the liquid level, some liquid may enter into the guide tube 220 from the gas reflux port. However, since the guide tube 220 has two gas reflux ports and the two gas reflux ports are arranged relatively, that part of liquid can easily flow out from the other gas reflux port along the straight guide tube 220 rather than enter into the gas outlet guiding tube 210. Of course, if the space in the liquid storage cavity 120 permits, the guide tube 220 may have more gas reflux ports. In such a case, the liquid that enters into the guide tube 220 from a gas reflux port can flow out from other gas reflux ports.

Preferably, the communication port 222 of the guide tube 220 is higher than the gas reflux ports 224 and 226. For example, the guide tube 220 may be inclined downward gradually from the communication port 222 toward the gas reflux ports 224 and 226, so that the liquid that enters via the gas reflux ports 224 and 226 can return to the liquid storage cavity 120. For example, the guide tube 220 may be inclined downward in a stepped form from the communication port 222 toward the gas reflux port 224 and 226. The guide tube 220 may be in any configuration, as long as it enables the communication port 222 to be higher than the gas reflux ports 224 and 226. The guide tube 220 is the highest at the communication port 222 of the guide tube 220. The guide tube 220 is the lowest at the gas reflux ports 224 and 226. Thus, even the liquid enters into the guide tube 220 from the gas reflux ports 224 and 226 of the guide tube 220 by accident, and it will flow back to the liquid storage cavity 120 rather than enter into the user interface.

Figure 7:
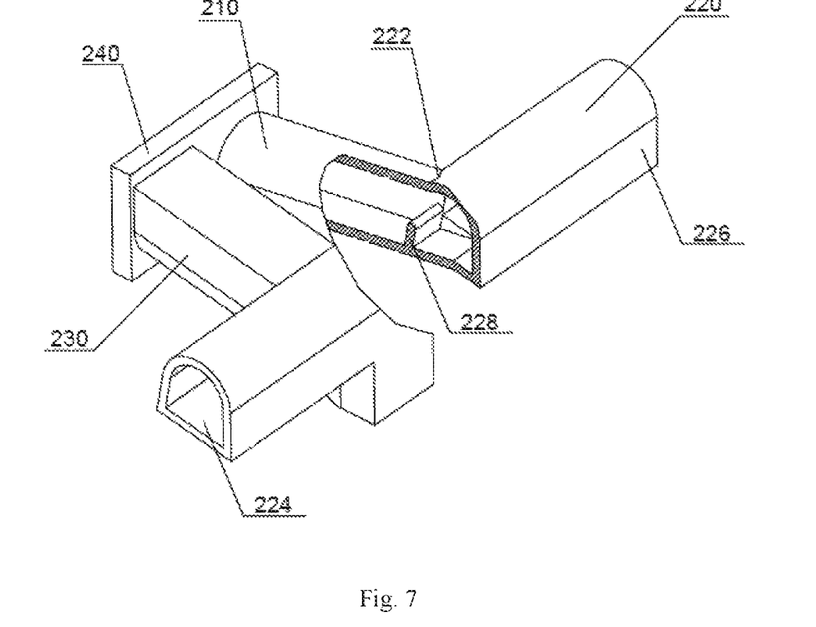
FIG. 7 is a schematic structural diagram of the gas guide tube assembly according to an embodiment of the present invention, wherein the gas guide tube assembly is cut away partially to show the internal structure of the gas guide tube assembly.

As described above, in the case that the gas inlet port 212 of the gas outlet guiding tube 210 is higher than the gas outlet port 214 of the gas outlet guiding tube 210, preferably a protective device is added. As shown in FIG. 7, the protective device may be a separating rib 228. The separating rib 228 may be disposed in the guide tube 220. The separating rib 228 may be disposed in the lower part of the flow path in the guide tube 220 to separate the lower flow path of the guide tube 220. The "flow path" comprises all fluid paths from each of the gas reflux ports of the guide tube 220 to the communication port 222. The separating rib 228 is configured to separate the lower part of each flow path of the guide tube 220. Thus, the fluid (including gas and liquid) can only flow through the upper part of each flow path in the guide tube 220, so that even if some liquid enters into the flow path in the guide tube 220 from any gas reflux port, the liquid will be blocked by the separating rib 228 and can't enter into the gas outlet guiding tube 210. Optionally, a separating rib 228 may be provided in each flow path from each gas reflux port to the communication port to block the lower flow path. However, preferably, as shown in FIG. 7, the separating rib 228 may be arranged at the communication port 222 of the guide tube 220. That is to say, the separating rib 228 is arranged at each flow path junction, i.e., the junction between the guide tube 220 and the gas outlet guiding tube 210. Thus, less separating ribs 228 may be arranged to attain the same technical effect, and thereby the structure of the product and manufacturing process can be simplified. It should be understood that the above-mentioned protective device may be arranged in the gas outlet guiding tube 210 where the gas inlet port 212 is lower than the gas outlet port 214.

The gas guide tube assembly provided in the present invention may be disposed in the liquid storage cavity of a humidifier, and the gas outlet port of a gas outlet guiding tube of the gas guide tube assembly communicates with a gas outlet of the liquid storage cavity. Since a guide tube is connected with the gas inlet port of a gas outlet guiding tube of the gas guide tube assembly, the gas is guided via the guide tube to flow into the gas inlet port of the gas outlet guiding tube, in addition, the guide tube has a plurality of gas reflux ports, so that the liquid will flow out via the other gas reflux ports even if the liquid flows in via one gas reflux port incurred by swaying of the liquid storage cavity, and thereby the possibility of liquid flowing into the gas inlet port of the gas outlet guiding tube is decreased. Furthermore, owing to the existence of the gas outlet guiding tube and the guide tube, the flow path of the gas in the liquid storage cavity is lengthened, so that the gas can be mixed extensively with the vapor produced through evaporation, and thereby the outflow gas has expected humidity and temperature.

In a preferred embodiment, the liquid storage device 10 further comprises a gas inlet guide tube 230. The gas inlet guide tube 230 is configured to guide the direction of the gas entering into the liquid storage cavity 120. The gas inlet guide tube 230 has a gas inlet port 232 and a gas outlet port

234, as shown in FIGS. 3A and 4. The gas inlet port 232 of the gas inlet guide tube 230 is higher than the gas outlet port 234 of the gas inlet guide tube 230. The gas inlet guide tube 230 is intended to be disposed in the liquid storage cavity 120 of the humidifier. The gas inlet port 232 of the gas inlet guide tube 230 is configured to directly or indirectly communicate with the second gas inlet 122 of the liquid storage cavity 120. The gas inlet port 232 of the gas inlet guide tube 230 may be connected to the first gas inlet 132 of the gas inlet cavity 130. In an embodiment in which there is no gas inlet cavity 130, the gas inlet port 232 may be directly connected to the second gas inlet 122. Preferably, the gas inlet port 232 of the gas inlet guide tube 230 may be removably connected to the first gas inlet 132 or the second gas inlet 122, so that it can be removed and replaced conveniently. For example, a socket may be arranged at the first gas inlet 132, and the gas inlet port 232 of the gas inlet guide tube 230 may be inserted into the socket, as shown in FIGS. 4 and 5. Thus, they can be connected via a socket joint. To ensure gas tightness of the connection, a sealing element 160 may be provided between them. In other embodiments that are not shown, the gas inlet port 232 of the gas inlet guide tube 230 may be connected to the first gas inlet 132 in a different way. Different possible connection means are not enumerated and described anymore here. The gas outlet port 234 of the gas inlet guide tube 230 extends into the liquid storage cavity 120, as shown in FIGS. 3A and 4-5. The gas inlet port 232 of the gas inlet guide tube 230 is higher than the gas outlet port 234 of the gas inlet guide tube, to guide the gas to flow in the direction to the liquid level, to avoid direct impact of the gas to the side wall of the liquid storage cavity 120, which may produce noise. Furthermore, since the gas outlet port 234 of the gas inlet guide tube 230 is relatively lower, even some liquid enters into the gas inlet guide tube 230 from the gas outlet port 234 by accident, the liquid will return to the liquid storage cavity 120, and thereby the liquid can be prevented from entering into the main unit. Owing to the existence of the gas inlet guide tube 230, the flow path of the gas in the liquid storage cavity 120 is lengthened, so that the gas can be mixed extensively with the vapor produced through evaporation, and thereby the outflow gas has expected humidity and temperature.

Further preferably, the opening of the gas outlet port 234 of the gas inlet guide tube 230 is downward. The opening of the gas outlet port 234 of the gas inlet guide tube 230 directly faces the liquid level to avoid impact with the side wall of the liquid storage cavity 120, which may generate noise. In addition, after the gas enters into the liquid storage cavity, it will be blocked at the liquid level and flow toward all sides in a generally uniform manner, so that the gas can be mixed extensively with the vapor produced through the evaporation. The gas outlet port 234 preferably is higher than the maximum fillable level of the liquid storage cavity 120. In that way, on one hand, the liquid can be prevented from entering into the gas inlet guide tube 230 from the gas outlet port 234; on the other hand, the gas can be prevented from entering into the liquid, which may produce gas bubbles and result in noise.

Preferably, the air guide tube assembly 200 further comprises a connector 240. The connector 240 fixes the gas outlet port 214 of the gas outlet guiding tube 210 and the gas inlet port 232 of the gas inlet guide tube 230 together. The connector 240 is further configured to connect the gas guide tube assembly 200 to the liquid storage cavity 120 of the humidifier. Thus, the gas outlet guiding tube 210 and the gas inlet guide tube 230 may be removed or assembled together, share the same sealing element 160, and share the same socket joint structure, and thereby the quantity of parts and components can be reduced.

The internal space of the liquid storage cavity 120 is usually limited. For an gas guide tube assembly 200 that includes a gas inlet guide tube 230, the directions of inclination of the gas outlet guiding tube 210 and the gas inlet guide tube 230 may be opposite to each other, as shown in FIGS. 4-5 and 7. Viewed from a side of the liquid storage cavity (generally in the extension direction of the guide tube 220), the gas outlet guiding tube 210 and the gas inlet guide tube 230 intersect with each other. The gas inlet port 212 of the gas inlet guide tube 210 is higher than the gas outlet port 234 of the gas inlet guide tube 230. Preferably, the gas outlet port 234 of the gas inlet guide tube 230 may be located below the guide tube 220. Thus, the utilization of the space in the liquid storage cavity may be optimized. Of course, the gas inlet port 212 of the gas outlet guiding tube 210 may be lower than or flush with the gas outlet port 234 of the gas outlet guiding tube 210, if the internal space of the liquid storage cavity 120 is large enough. The gas outlet port 214 of the gas outlet guiding tube 210 and the gas inlet port 232 of the gas inlet guide tube 230 may be essentially at the same level; of course, they may be at different elevations if required.

Figure 6:
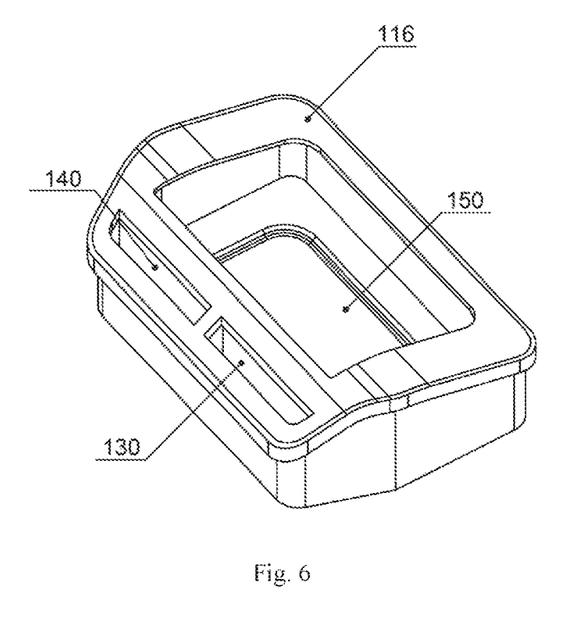
FIG. 6 is a schematic structural diagram of the lower casing assembly according to an embodiment of the present invention.
Figure 8:
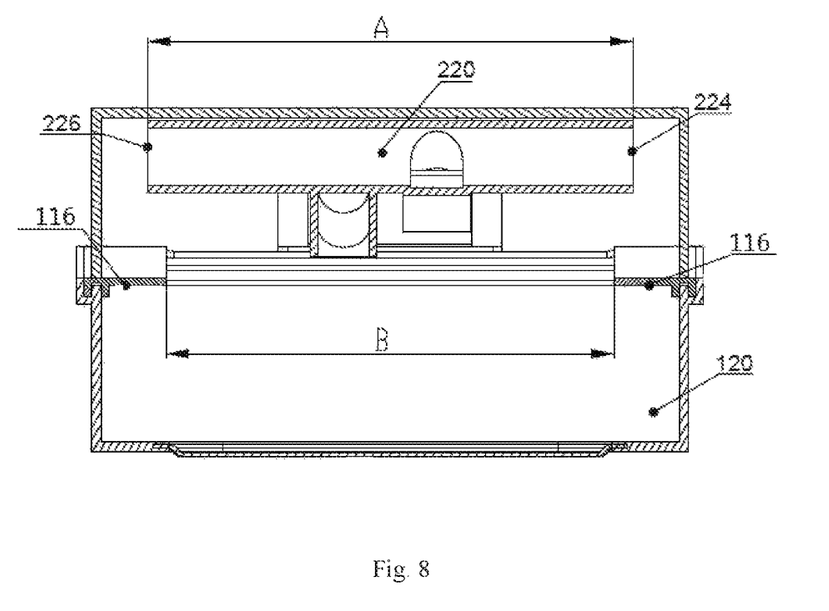
FIG. 8 is a sectional view of the liquid storage device along the line C-C in FIG. 3B, illustrating the guide tube.
Figure 9:
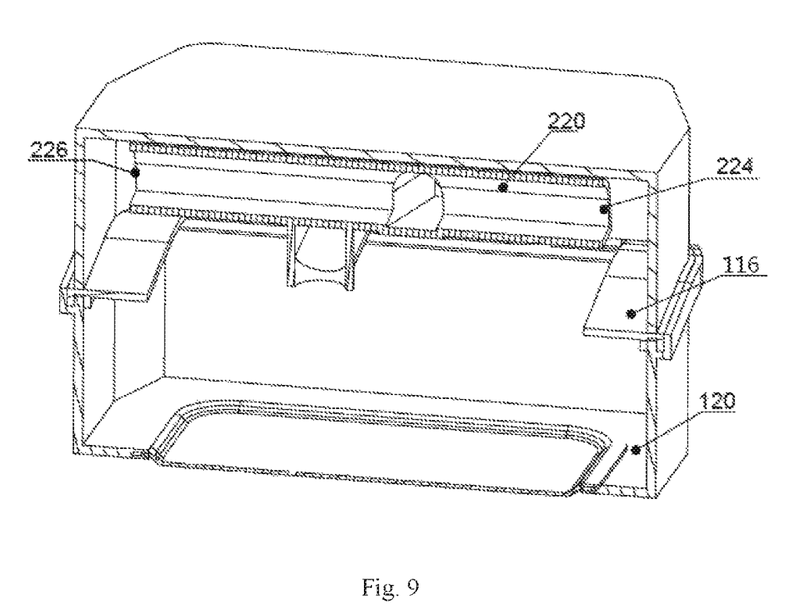
FIG. 9 is a schematic structural diagram of the liquid storage device along the line C-C in FIG. 3B.

Furthermore, as shown in FIGS. 6 and 8-9, the inner circumference of the seal ring 116 extends into the liquid storage cavity 120. The gas reflux ports 224 and 226 of the guide tube 220 are right above the portion of the seal ring 116 that extends into the liquid storage cavity 120. That is to say, the downward projection of the gas reflux ports 224 and 226 of the guide tube 220 in the vertical direction fall on the portion of the seal ring 116 that extend into the liquid storage cavity 120. For the liquid storage cavity 120 that has uniform width in the vertical direction as shown in the figures, it is deemed that the distance from the inner edge of the seal ring 116 to the side wall of the liquid storage cavity 120 is greater than the distance from the gas reflux ports 224 and 226 to the side wall of the liquid storage cavity. More specifically, in the embodiment in which the guide tube 220 is a straight tube as shown in the figures, suppose the spacing between the gas reflux ports 224 and 226 is defined as A and the spacing between the portions of the seal ring 116 that extend into the liquid storage cavity 120 is defined as B, then A is greater than B. However, it is understood that the gas reflux ports 224 and 226 advantageously is not close to the side wall of the liquid storage cavity 120 to avoid adverse to the gas flow. However, in a case that there are a great number of gas reflux ports, there is little adverse effect to the gas flow even if the gas reflux ports are close to the side wall. Therefore, those skilled in the art may reasonably select the number of the gas reflux ports, the distance from the gas reflux ports to the side wall of the liquid storage cavity, and the like, on the basis of the ideal in the present invention. Since the liquid is blocked by the portion of the seal ring 116 that extends into the liquid storage cavity 120 and can't sway into the gas reflux ports 224 and 226, the liquid hardly enters into the guide tube 220. Even if some water enters into the guide tube 220 in the case of vehement sway, the liquid can flow out easily since the guide tube 220 has a plurality of gas reflux ports.

Please see FIG. 1 again, the second gas inlet 122 and the second gas outlet 124 are arranged on the same side surface (i.e., the first side surface 1112) of the liquid storage device 10. When a humidifier having the liquid storage device 10 is installed into the main unit, the second gas inlet 122 and the second gas outlet 124 usually face the main unit to shorten the gas path. That is to say, the first side surface 1112 on which the second gas inlet 122 and the second gas outlet 124 are arranged will enter into the main unit first. For the convenience of installation, the first side surface 1112 is connected to the adjacent side surface 1116 via the bevel surface 1114. The side surface opposite to the side surface 1116 is not shown in FIG. 1.

According to another aspect of the present invention, the present invention provides a humidifier that comprises a heating element and the liquid storage device described above, wherein, the heating element is disposed under the liquid storage cavity of the liquid storage device. For the heating element and the liquid storage device, please see the description in the corresponding portions in the above text. They are not described further for brevity.

According to a still another aspect of the present invention, the present invention provides a ventilator that comprises the humidifier described above.

The ventilator further comprises a main unit and a breathing mask that communicate with the humidifier. In the ventilator according to the present invention, the gas inlet cavity of the liquid storage device of the humidifier can prevent the liquid from over-flowing via the second gas inlet into the main unit and resulting in damage of the main unit, and the gas outlet cavity can prevent the liquid from overflowing via the second gas outlet into the breathing mask, and thereby prevent water inhalation into the user. Thus it is seen: the ventilator provided in the present invention attains an excellent overflow prevention effect, and thereby can prolong the service life of the main unit and improve the comfort of the user during use.

While the present invention is described above in embodiments, it should be appreciated that the above embodiments are provided only for an illustration and description purpose rather than intended to limit the present invention to the scope defined by the embodiments. Those skilled in the art should appreciate that the present invention is not limited to the above-mentioned embodiments. More variations and modifications can be made on the basis of the teaching provided in the present invention, and those variations and modifications shall be deemed as falling in the claimed scope of protection of the present invention. The scope of protection of the present invention is only defined by the attached claims and their equivalents.

The invention claimed is:

1. A gas guide tube assembly for a humidifier, comprising:
a gas outlet guiding tube having a gas inlet port and a gas outlet port;
a guide tube having a communication port that communicates with the gas inlet port of the gas outlet guiding tube and a plurality of gas reflux ports that communicate with the communication port; and
a gas inlet guide tube having a gas inlet port and a gas outlet port, wherein in a first direction, the gas inlet port of the gas inlet guide tube is higher than the gas outlet port of the gas inlet guide tube.

2. The gas guide tube assembly according to claim 1, wherein, in the first direction, the gas inlet port of the gas outlet guiding tube is higher than the gas outlet port, and level with the gas reflux ports.

3. The gas guide tube assembly according to claim 1, wherein, in the first direction, the communication port of the guide tube is higher than the gas reflux ports, and/or the gas inlet port of the gas outlet guide tube is lower than the gas outlet port of the gas outlet guide tube.

4. The gas guide tube assembly according to claim 1, wherein, the guide tube is a straight guide tube having two gas reflux ports.

5. The gas guide tube assembly according to claim 1, wherein, the gas outlet port of the gas inlet guide tube is below the guide tube, and the opening of the gas outlet port of the gas inlet guide tube is downward.

6. The gas guide tube assembly according to claim 1, wherein, the gas guide tube assembly further comprising a connector, the connector fixes the gas outlet port of the gas outlet guide tube and the gas inlet port of the gas inlet guide tube together, and is configured to connect the gas guide tube assembly to a liquid storage cavity of the humidifier.

7. The gas guide tube assembly according to claim 1, wherein the guide tube is provided with a separating rib therein, the separating rib is arranged in a lower part of a flow path in the guide tube and configured to separate a lower flow path in the guide tube.

8. A liquid storage device for a humidifier, comprising:
a casing assembly with an liquid storage cavity formed internally, the liquid storage cavity having a gas inlet and a gas outlet; and
a gas guide tube assembly comprising
a gas outlet guiding tube having a gas inlet port and a gas outlet port; and
a guide tube having a communication port that communicates with the gas inlet port of the gas outlet guiding tube and a plurality of gas reflux ports that communicate with the communication port,
wherein the gas guide tube assembly is disposed in the liquid storage cavity and connected to the casing assembly, the gas outlet port of the gas outlet guide tube of the gas guide tube assembly communicates with the gas outlet, and the gas reflux ports of the gas guide tube assembly are higher than the maximum tillable level in the liquid storage cavity.

9. The liquid storage device according to claim 8, wherein, a gas inlet cavity and a gas outlet cavity are formed in the casing assembly, wherein,
the gas inlet cavity has a first gas inlet communicating with the liquid storage cavity and a second gas inlet communicating with the exterior of the liquid storage device; and
the gas outlet cavity has a first gas outlet communicating with the liquid storage cavity and a second gas outlet communicating with the exterior of the liquid storage device.

10. The liquid storage device according to claim 9, wherein, both the gas inlet cavity and the gas outlet cavity are adjacent to the liquid storage cavity.

11. The liquid storage device according to claim 9, wherein, the casing assembly comprises an upper casing assembly and a lower casing assembly, the upper casing assembly is removably or pivotally connected to the lower casing assembly, and the upper casing assembly and the lower casing assembly jointly form the liquid storage cavity, the gas inlet cavity, and the gas outlet cavity.

12. The liquid storage device according to claim 11, wherein, the upper casing assembly has a first fitting surface, the lower casing assembly has a second fitting surface, and the first fitting surface and the second fitting surface are asymmetric curved surfaces fitted with each other.

13. The liquid storage device according to claim 12, wherein, both the first fitting surface and the second fitting surface comprise a first bevel surface and a second bevel surface that are inclined downward from a central part to opposite sides and are arranged asymmetrically.

14. The liquid storage device according to claim 9, wherein, the gas inlet cavity and the gas outlet cavity are formed by separating with a first baffle plate and a second baffle plate in the casing assembly, wherein the first baffle plate is disposed between the gas inlet cavity, the gas outlet cavity and the liquid storage cavity, the second baffle plate is disposed between the gas inlet cavity and the gas outlet cavity, and both the first gas inlet and the first gas outlet are arranged on the first baffle plate.

15. The liquid storage device according to claim 9, wherein, the second gas inlet is higher than the first gas inlet, and/or the second gas outlet is higher than the first gas outlet.

16. The liquid storage device according to claim 9, wherein, the second gas inlet and the second gas outlet are arranged on a first side surface of the liquid storage device, and the first side surface is connected via a bevel surface to a side surface of the liquid storage device that is adjacent to the first side surface.

17. The liquid storage device according to claim 11, wherein, the casing assembly comprises a seal ring disposed between the upper casing assembly and the lower casing assembly, the inner circumference of the seal ring extends into the liquid storage cavity, and the gas reflux ports of the guide tube are right above the portion of the seal ring that extends into the liquid storage cavity.

18. A ventilator comprising a heating element and the liquid storage device according to claim 8, wherein, the heating element is disposed under the liquid storage cavity of the liquid storage device.

\* \* \* \* \*